United States Patent
Lai et al.

(10) Patent No.: US 10,045,836 B2
(45) Date of Patent: Aug. 14, 2018

(54) FLEXIBLE ORTHODONTIC SPLINT

(71) Applicant: 3M INNOVATIVE PROPERTIES COMPANY, St. Paul, MN (US)

(72) Inventors: Ming-Lai Lai, Arcadia, CA (US); Sung Kim, Montebello, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 99 days.

(21) Appl. No.: 14/383,398

(22) PCT Filed: Feb. 28, 2013

(86) PCT No.: PCT/US2013/028163
§ 371 (c)(1),
(2) Date: Sep. 5, 2014

(87) PCT Pub. No.: WO2013/134031
PCT Pub. Date: Sep. 12, 2013

(65) Prior Publication Data
US 2015/0044625 A1    Feb. 12, 2015

Related U.S. Application Data

(60) Provisional application No. 61/606,787, filed on Mar. 5, 2012.

(51) Int. Cl.
*A61C 7/16* (2006.01)
*A61C 5/00* (2017.01)
(Continued)

(52) U.S. Cl.
CPC ............... *A61C 7/16* (2013.01); *A61C 5/007* (2013.01); *A61C 7/00* (2013.01); *A61C 7/12* (2013.01)

(58) Field of Classification Search
CPC .... A61C 7/16; A61C 7/00; A61C 7/10; A61C 5/007; A61C 7/12
(Continued)

(56) References Cited

U.S. PATENT DOCUMENTS

| | | | |
|---|---|---|---|
| 4,015,334 A | 4/1977 | Moss | |
| 4,332,563 A * | 6/1982 | Weissman | A61C 5/00 403/229 |

(Continued)

FOREIGN PATENT DOCUMENTS

| | | |
|---|---|---|
| EP | 1449494 | 8/2004 |
| WO | WO 2002-19939 | 3/2002 |
| WO | WO 2008-045932 | 4/2008 |

OTHER PUBLICATIONS

International Search Report for PCT International Application No. PCT/US2013/028163, dated Jun. 27, 2013, 6pgs.

*Primary Examiner* — Nicholas Lucchesi

(57) ABSTRACT

Provided is an orthodontic splint and related methods, which use two or more bonding pads and a flexible connector beam that deflects in response to stress, effectively reducing the amount of stress felt by the adhesive. The connector beam has a non-uniform cross-section along its length, thereby shifting the maximum stress away from the ends of the beam and toward the midpoint of the beam. Further, the connector beam attached to each base along locations remote from the outer edge of the base. These splint configurations can decrease the likelihood of bond failure and improve fatigue performance by causing stress, and associated strain, encountered during treatment to be spread more evenly along the length of the beam.

17 Claims, 5 Drawing Sheets

(51) Int. Cl.
*A61C 7/00* (2006.01)
*A61C 7/12* (2006.01)

(58) Field of Classification Search
USPC .......................................... 433/9, 18, 24, 215
See application file for complete search history.

(56) References Cited

U.S. PATENT DOCUMENTS

| | | | | |
|---|---|---|---|---|
| 4,412,818 A * | 11/1983 | Thomson | ................. | A61C 5/00 433/1 |
| 4,433,960 A * | 2/1984 | Garito | ..................... | A61C 7/00 433/180 |
| 4,516,938 A | 5/1985 | Hall | | |
| 4,609,350 A | 9/1986 | Krause | | |
| 5,087,202 A * | 2/1992 | Krenkel | ................. | A61C 5/007 433/19 |
| 5,184,955 A * | 2/1993 | Baer | ..................... | A61C 5/007 433/215 |
| 5,505,616 A | 4/1996 | Harwell | | |
| 5,538,422 A | 7/1996 | Arndt | | |
| 5,669,377 A * | 9/1997 | Fenn | ........................ | A62B 9/06 128/200.24 |
| 5,785,520 A | 7/1998 | Carano | | |
| 5,967,772 A | 10/1999 | Gray | | |
| 6,027,340 A | 2/2000 | Chun | | |
| 6,776,614 B2 | 8/2004 | Wiechmann | | |
| 8,486,122 B2 * | 7/2013 | Nakano | .................. | A61B 17/24 606/322 |
| 2003/0180689 A1 * | 9/2003 | Arx | ........................... | A61C 5/00 433/215 |
| 2004/0048222 A1 | 3/2004 | Froster | | |
| 2004/0166477 A1 * | 8/2004 | Lans | ...................... | A61C 5/007 433/215 |
| 2005/0181332 A1 | 8/2005 | Sernetz | | |
| 2006/0078849 A1 | 4/2006 | Parks | | |
| 2006/0093984 A1 * | 5/2006 | Rosenberg | ............... | A61C 7/12 433/6 |
| 2010/0015565 A1 * | 1/2010 | Carrillo Gonzalez | ... | A61C 5/00 433/7 |
| 2012/0028221 A1 * | 2/2012 | Williams | ............... | A61C 5/007 433/215 |

\* cited by examiner

FLEXIBLE ORTHODONTIC SPLINT

CROSS REFERENCE TO RELATED APPLICATIONS

This application is a national stage filing under 35 U.S.C. 371 of PCT/US2013/028163, filed Feb. 28, 2013, which claims priority to provisional Application No. 61/606,787, filed Mar. 5, 2012, the disclosure of which is incorporated by reference in its/their entirety herein.

FIELD

The provided devices and methods are related to accessories used in orthodontic treatment. In particular, the provided devices and methods are related to splints used in orthodontic treatment.

BACKGROUND

Orthodontics is a specialized profession in dentistry concerned with the precise application of forces to teeth, thereby guiding them into proper positions. Such treatment has many potential benefits, including improvement to bite function, maintenance of dental hygiene, and facial aesthetics. Fixed appliance therapy is one common type of orthodontic treatment which involves bonding tiny slotted appliances, called brackets, to the teeth. After bonding, a resilient arch-shaped wire (or "archwire") is placed in the slots of the brackets to begin treatment. Although the archwire is initially deflected from its original shape when installed, the wire imparts gentle therapeutic forces over time, thereby progressively moving crooked teeth toward their proper locations in the mouth.

The treating professional will sometimes use a device called an orthodontic splint to achieve a particular treatment result. The use of a splint, or "splinting," involves joining together two or more teeth to immobilize them relative to each other. Because this effectively enlarges the root surface area engaged with the jawbone, this has the effect of providing greater anchorage by increasing the resistance to forces applied to the teeth. Achieving proper anchorage during treatment is generally important to resist reactive forces generated as a result of the activation of an orthodontic appliance, such as an archwire, and avoid undesirable tooth movement. Splinting can also be useful when treatment is confined to certain teeth segments (for example, in cuspid-to-cuspid, or "3×3" treatment, or bicuspid-to-bicuspid, or "5×5" treatment), where it can be useful to connect the first and second bicuspid teeth or first molar and second molar teeth.

SUMMARY

A conventional banded orthodontic splint, shown attached to an orthodontic bracket in FIG. 1, can have a very low profile and provide a high level of patient comfort. This type of splint also has significant drawbacks. First, these splints can be highly rigid along directions coplanar with the underlying tooth surface, which tends to localize stresses on the splint. These splints are also limited in their ability to absorb energy from bite forces, thus causing this energy to be transmitted directly to the bonding joints. Second, the periodontal ligament extending around each tooth is, on average, around 0.15 to 0.20 millimeters thick. As a result, the teeth are naturally mobile and can move significantly relative to each another during treatment and especially during mastication. This relative movement of teeth imposes additional stress on both the bonding adhesive and splint, often resulting in either shear-peel type bond failure or fracture of the splint itself during treatment. This will often require re-fabrication and bonding of a new splint, which is a substantial nuisance to the treating professional.

This problem can be somewhat alleviated by using a splint with two or more bonding pads and a flexible connector that deflects in response to the relative tooth movement, effectively reducing the amount of stress felt by the adhesive. It was found, however, that the use of a flexible connector alone does not sufficiently answer the problem. For example, stress can still concentrate near the ends of the connector, and such stress can induce either splint or adhesive failure. While the maximum stress can be reduced by increasing the length or reducing the cross-sectional area of the connector, this can have the effect of attenuating the mechanical coupling between the pads to the point where the functionality of the splint is compromised. Such adjustments can also adversely affect the overall profile of the splint, leading to decreased patient comfort.

The provided orthodontic splints can overcome this dilemma by using a connector beam between two or more bases that is non-prismatic; in other words, the connector beam does not have uniform cross-section throughout its length. By tapering the cross-section from a relatively large cross-section near one base to a relatively smaller cross-section near the beam midpoint, it is possible to redistribute the stress field in the splint more uniformly. Redistributing stresses along the splint not only can decrease the likelihood of bond failure, but also improve fatigue performance since the stress (and associated strain) is spread more evenly along the length of the connector. A surprising enhancement in robustness can also be achieved by having the connector beam being joined to each base at a location remote from the outer edge of the base.

In one aspect, an orthodontic splint is provided. The orthodontic splint comprises: a first base and second base, each base having a bonding surface for attachment to a respective tooth and an outer edge extending along at least a portion of the bonding surface as viewed from a direction generally perpendicular to the bonding surface; and a resilient, elongated connector beam having a cross-sectional dimension that generally increases with increasing proximity to the nearer of the first or second base, the connector beam attached to each base along locations remote from the outer edge of the base.

In another aspect, an orthodontic splint is provided comprising: a first base and second base, each base having a bonding surface for attachment to a respective tooth surface and an outer edge extending along at least a portion of the bonding surface as viewed from a direction generally perpendicular to the bonding surface; and a resilient, elongated connector beam having a longitudinal midpoint and a cross-sectional dimension that generally decreases when approaching the midpoint from either the first or second base, the connector beam attached to each base in a position remote from the outer edge of the base.

In still another aspect, an orthodontic splint is provided comprising: a first base and second base, each base having a bonding surface for attachment to a respective tooth surface and an outer edge extending along at least a portion of the bonding surface as viewed from a direction generally perpendicular to the bonding surface; and an elongated connector beam resiliently coupling the first and second bases to each other and having a cross-sectional dimension that generally increases with increasing proximity to the nearer of the first or second base, the connector beam extending outwardly away from each base at an angle ranging from 10 to 90 degrees relative to a tangent plane where the longitudinal axis of the connector beam intersects a respective outer surface of the base.

In yet another aspect, a method of maintaining a fixed spatial relationship between a first and second tooth during orthodontic treatment is provided. The method comprises: coupling a first base to the first tooth; and coupling a second base to the second tooth, wherein the first and second bases are resiliently interconnected by an elongated connector beam with ends extending outwardly away from the tooth surface and a cross-sectional dimension that generally decreases toward the midpoint of the connector beam, whereby stress is delocalized along the length of the beam.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

Provided herein are splints for use in orthodontic treatment. In preferred embodiments, the splints provides anchorage as part of a system of appliances that are bonded to some or all of the central, lateral, cuspid, bicuspid, and molar teeth of a dental arch and cooperate with a suitable archwire for moving teeth to proper respective locations. The splints couple two or more teeth to each other and may have a configuration for attachment to either facial or lingual surfaces of the teeth, and can be adapted for use on either the upper or lower arches. While embodiments described herein are directed to lingual splints, it should be understood that similar features and benefits may also apply for labial splints with references to facial and lingual directions reversed.

The provided splints may have a universal configuration reflecting normative tooth shapes in the patient population. Alternatively, the splints can be custom manufactured according to the shapes of a particular patient's teeth, and thus may have configurations that differ substantially from one patient to the next. Some of these possibilities are further explored in the sections below. While particular splint configurations and features are shown herein by way of illustration and example, however, these embodiments should not be construed as unduly limiting the scope of the invention.

Figure 2:
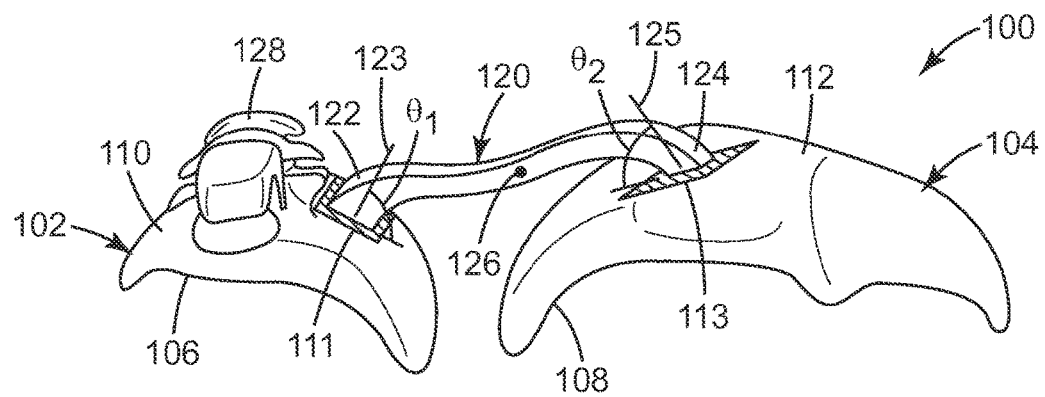
FIG. 2 is an occlusal perspective view of a lingual orthodontic splint according to one embodiment, looking at the occlusal and lingual sides.
Figure 3:
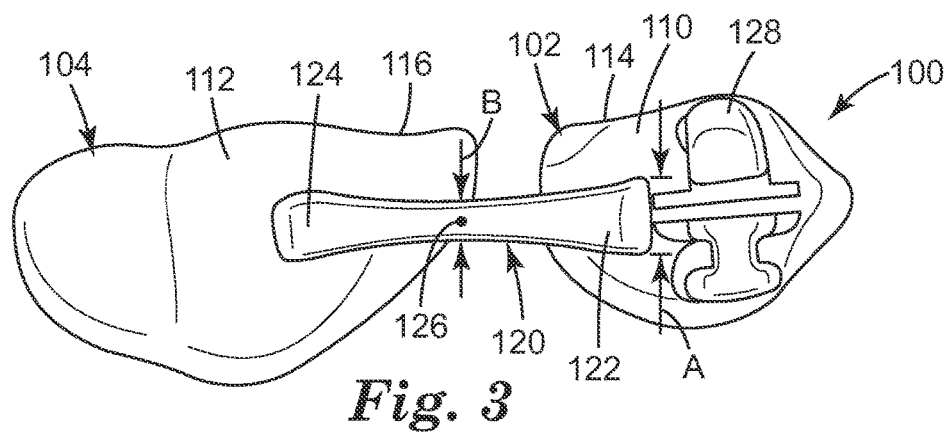
FIG. 3 is a lingual view of the splint in FIG. 2, looking at its lingual side.

A lingual splint, according to one exemplary embodiment, is shown in FIGS. 2-3 and broadly designated by the numeral 100. The splint 100 has a mesial base 102 and a distal base 104. Each of the bases 102, 104 has a bonding surface 106, 108 for attachment to a corresponding tooth. As shown in FIG. 2, the bases 102, 104 and respective bonding surfaces 106, 108 are customized to substantially match the lingual contours of the first and second bicuspid teeth of a patient. The bonding surfaces 106, 108 can have a surface structure that assists in providing mechanical retention with a suitable bonding adhesive. The surface structure can improve adhesion, for example, by forming a mechanical lock or chemical bond with a suitable adhesive disposed between the bonding surface 106, 108 and the tooth surface. The surface structure may include holes, grooves, particles, recesses, undercuts, a micro-etched surface, a chemical bond enhancement material, or any other structure, material or combination thereof.

The bases 102, 104 can extend over a significant portion of its associated tooth surface to provide for adhesion over a larger surface area and a stronger overall bond. Although not shown here, one or both of the bases 102, 104 could even extend entirely around the tooth, resulting in a banded appliance. The bases 102, 104 also have respective outer surfaces 110, 112 opposite the bonding surfaces 106, 108 and facing the lingual direction. Preferably, the outer surfaces 110, 112 substantially match the contours of the underlying teeth surfaces, giving the splint 100 a low overall profile for enhanced patient comfort.

Each of the bases 102, 104 also has a respective outer edge 114, 116 (shown in FIG. 3) that extending along the periphery of the bonding surfaces 106, 108 as viewed from a direction generally perpendicular to the surfaces 106, 108. As shown in the embodiment of FIG. 3, each outer edge 114, 116 fully surrounds its respective surface 106, 108.

An elongated connector beam 120 connects the mesial and distal bases 102, 104 to each other. The connector beam 120 has a mesial end 122 and a distal end 124 and a longitudinal midpoint 126. In a preferred embodiment, the connector beam 120 is made from a flexible material that allows the splint 100 to visibly deflect, or "flex," within its elastic limit in response to usual forces encountered during orthodontic treatment. Optionally, the connector beam 120 is also resilient along essentially its entire length, such that the beam 120 substantially returns to its original shape when relaxed. The connector beam 120 acts as a "shock absorber" that allows the mesial and distal bases 102, 104 to shift relative to each other during orthodontic treatment without inducing a significant degree of permanent deformation in either the bases 102, 104 or the connector beam 120. This can be beneficial to the treating professional because it allows two (or more) teeth to be joined together to provide increased anchorage, while tolerating a small degree of relative movement that naturally occur between teeth as a result of chewing forces and treatment mechanics.

The mesial and distal ends 122, 124 are joined to the respective outer surface 110, 112 of the bases 102, 104 along locations remote from (or away from) the outer edges 114, 116. By spacing the joint between the connector beam 120 and each base 102, 104 to locations remote from the outer edge 114, 116, the stress on the adhesive can be moved away from the edges of the bonding interface, where the bond between the tooth and the splint 100 is most vulnerable to shear-peel failure. As will be later shown in the Examples section, this aspect was found to significantly reduce the likelihood of shear-peel failure of the splint 100.

As further shown in FIGS. 2-3, the connector beam 120 has a generally rectangular cross-section as defined along reference planes perpendicular to the longitudinal axis of the connector beam 120. In a preferred embodiment, the long axis of the rectangular cross-section is aligned along a generally occlusal-gingival direction. Optionally, the rectangular connector beam 120 is canted so that it lies approximately parallel with the underlying bonding surfaces 106, 108 in consideration with the inclination of the teeth to which the splint 100 is bonded. Such alignment can reduce facial-lingual height, thereby reducing the overall profile of the splint 100 and promoting patient comfort.

Figure 1:
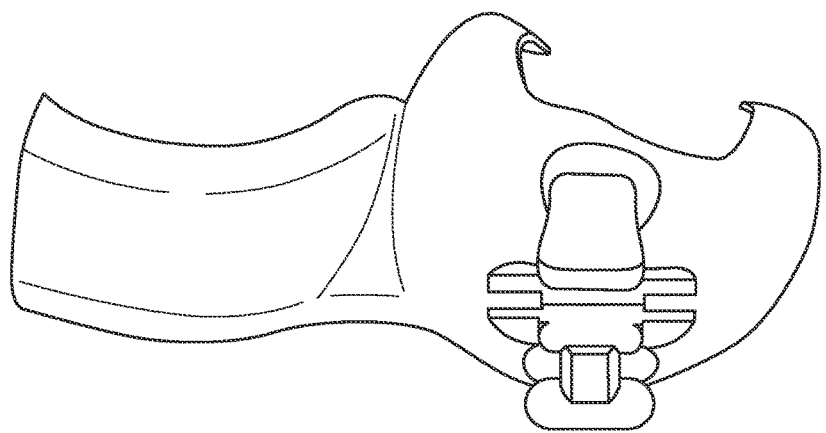
FIG. 1 is an occlusal lingual view of a conventional lingual orthodontic splint bonded to a test fixture, looking at its lingual side.

Unlike the banded splint configuration shown in FIG. 1, the splint 100 has a cross-section whose size and shape vary along the longitudinal axis of the connector beam 120. In the present instance, the connector beam 120 has a cross-sectional dimension that varies along two orthogonal axes. In FIG. 2, for example, the facial-lingual thickness of the connector beam 120 generally increases with increasing proximity to the nearest mesial or distal end 122, 124, and generally decreases when approaching the midpoint 126 from either the first or second base 102, 104. Stated another way, the cross-sectional dimension generally increases with increasing proximity to the nearer of the first or second base 102, 104. This is also shown in FIG. 3, in which the splint has its largest gingival-occlusal dimension "A" toward the ends 122, 124 and its smallest gingival-occlusal dimension "B" toward the midpoint 126.

In some embodiments, the ratio between a cross-sectional dimension of the connector beam 120 at its widest point and the cross-sectional dimension at its narrowest point is at least 1, at least 1.25, at least 1.5, or at least 1.75. In some embodiments, the ratio between a cross-sectional dimension of the connector beam 120 at its widest point and the cross-sectional dimension at its narrowest point is at most 3, at most 2.5, at most 2, or at most 1.75. In some embodiments, the cross-sectional dimension itself at its narrowest point is at least 0.18 millimeters, at least 0.4 millimeters, or at least 0.5 millimeters. In some embodiments, the cross-sectional dimension at its narrowest point is at most 1.4 millimeters, at most 1.1 millimeters, or at most 0.8 millimeters.

It can be advantageous for the facial-lingual dimension of the connector beam 120 to vary over a narrower range compared with the occlusal-gingival direction. In some embodiments, for example, the facial-lingual thickness of the connector beam 120 can be essentially uniform throughout its length while the occlusal-gingival thickness varies substantially along its length. Greater uniformity in thickness can allow the splint 100 to have a lower overall profile, a feature that could advantageously enhance patient comfort by reducing the extent to which the splint 100 impinges against the cheek of the patient.

As further shown in FIGS. 2-3, an orthodontic bracket 128 is joined to the mesial base 102 of the splint 100, providing options for engagement with an archwire, force module (such as a power chain or elastic), trans-palatal device or other ancillary orthodontic appliance. Optionally, the bracket 128 and splint 100 have a unitary construction and are manufactured as a unitary component. The bracket 128 has a slot for accommodating an archwire during the course of treatment. By fastening two or more teeth together, the splint 100 can provide enhanced anchorage when an archwire is activated in the slot of the bracket 128. If desired, anchorage can be further improved by incorporating one or more additional bonding bases into the splint 100, thereby leveraging the collective anchorage of three or more teeth.

The shape of the connector beam 120 can impart significant and unexpected advantages to the splint 100. First, by having a cross-sectional dimension that is enlarged near the ends 122, 124 and reduced near the midpoint 126, the principal stresses on the splint 100 are delocalized, or distributed more evenly, along the length of the connector beam 120 as the teeth move relative to each other. This has the effect of lowering the principal stress at the ends 122, 124 where the adhesive/appliance and adhesive/tooth interface present weak boundary layers where debonding of the splint 100 can occur. Second, the distribution of stress over an extended portion of the connector beam 120 can provide superior fatigue resistance. As a result, the splint 100 can display dramatically improved robustness over previous splint configurations disclosed in the art.

Optionally and as shown, the ends 122, 124 of the connector beam 120 extend outwardly from the bases 102, 104 along a direction approximately normal to planes 111, 113 tangent to the underlying outer surfaces 110, 112 (in FIG. 3, for example, the tangent planes 111, 113 are defined where the instantaneous longitudinal axis 123, 125 of the connector beam 120 intersects with each outer surface 110, 112). Referring to FIG. 2, the ends 122, 124 (as represented by the longitudinal axes 123, 125) extend outwardly at respective angles $\theta_1$ and $\theta_2$ relative to the tangent planes 111, 113, where $\theta_1$ is approximately 90 degrees and $\theta_2$ is somewhat less than 90 degrees.

Advantageously, this configuration can distribute principal stresses evenly along the cross-section of the connector beam 120 where each end 122, 124 is joined with its base 102, 104, and reduce the likelihood of shear-peel failure at the joint connecting the connector beam 120 to the bases 102, 104. Such a construction can also provide a minimal amount of facial-lingual separation between the connector beam 120 and the underlying bases 102, 104 to facilitate manufacturing of the splint 100, for example, by microcasting.

In some embodiments, each end of the connector portion extends outwardly away from each base 102, 104 at an angle $\theta$ of at least 10 degrees, at least 30 degrees, or at least 70 degrees, relative to a tangent plane 111, 113 where the longitudinal axis of the connector beam 120 intersects respective outer surface 110, 112. In some embodiments, each end of the connector portion extends outwardly away from each base 102, 104 at an angle $\theta$ of up to 80 degrees, up to 85 degrees, or up to 90 degrees, relative to the tangent plane 111, 113 above. The connector beam 120 need not extend along a path that continually travels away from one base 102, 104 and toward the other. For example, the connector beam 120 could initially extend from base 102 in a direction away from the base 104, then subsequently bend back toward base 104.

Figure 4:
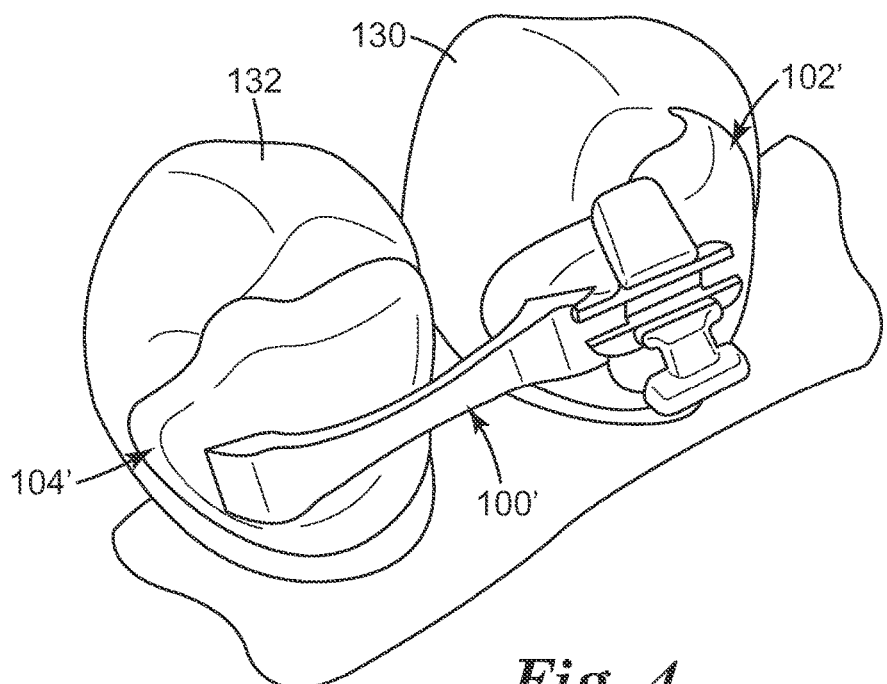
FIG. 4 is a perspective view of a splint according to another embodiment bonded to adjacent bicuspid teeth, looking at the occlusal and lingual sides.
Figure 5:
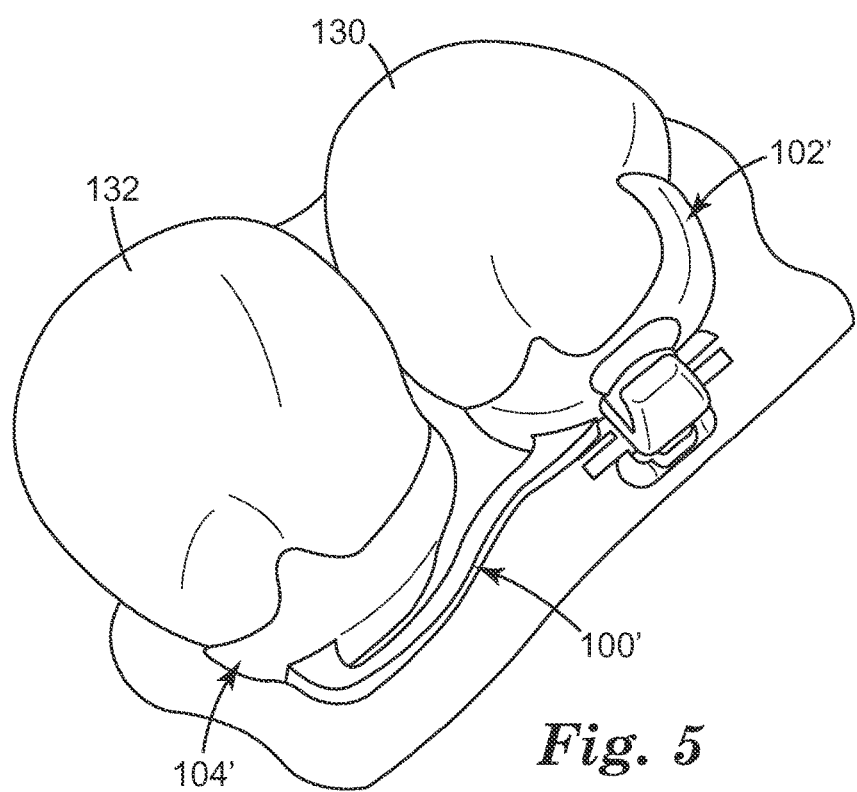
FIG. 5 is a perspective view of the splint of FIG. 4 bonded to adjacent bicuspid teeth, looking at its occlusal side.
Figure 6A:
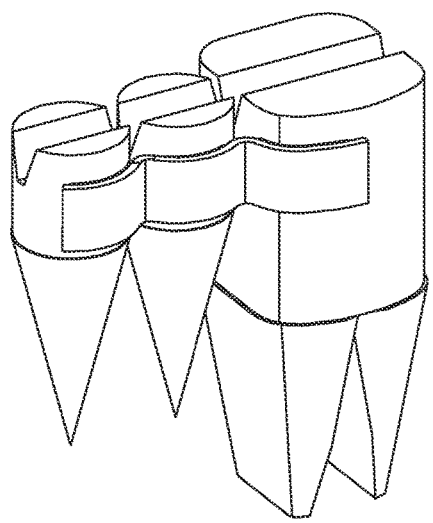
FIGS. 6(a)-(g) shows six three-dimensional solid models of splints provided as inputs for finite element analysis.
Figure 6B:
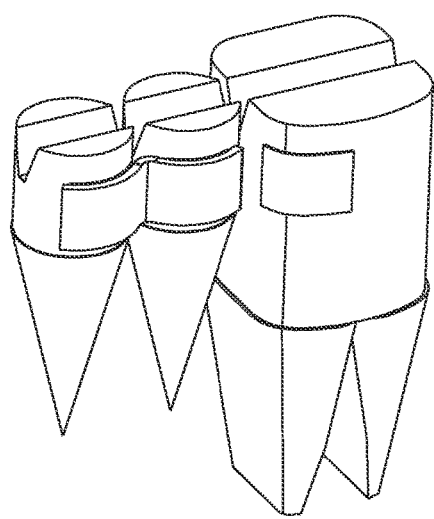
Figure 6C:
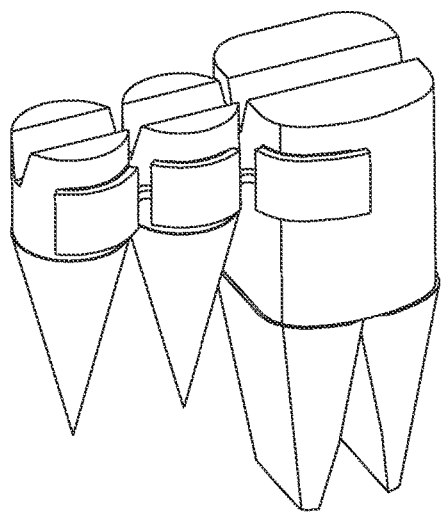
Figure 6D:
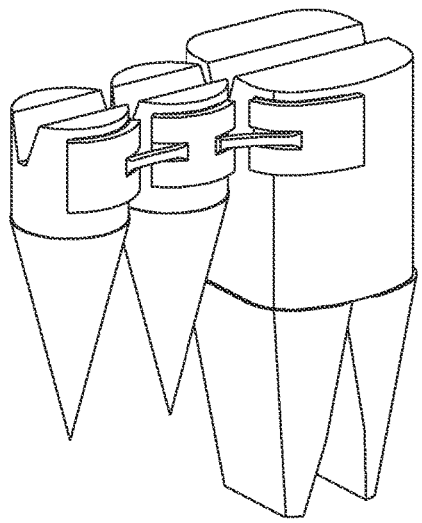
Figure 6E:
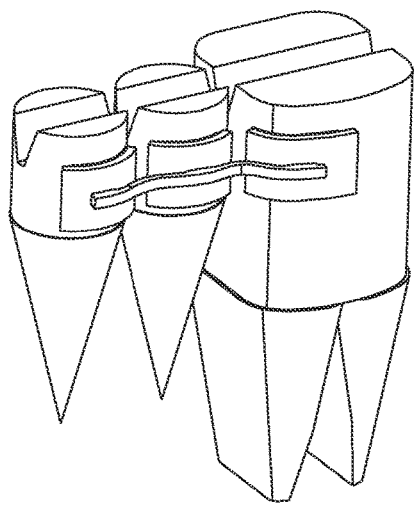
Figure 6F:
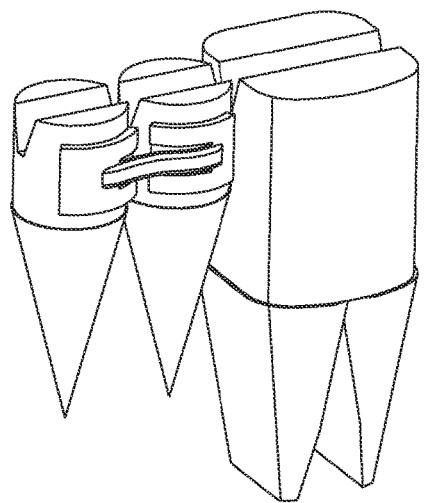
Figure 6G:
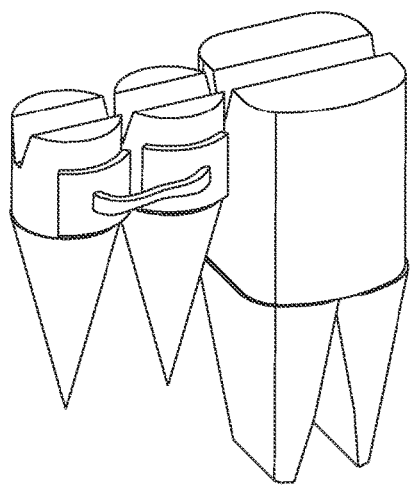

FIGS. 4-5 present views of a splint 100' as it would appear when bonded to the lower first bicuspid 130 and second bicuspid 132 teeth of a patient. A connector beam 120', having outer ends that extend outwardly away from the surface of each tooth 130, 132, resiliently interconnects respective bases 102', 104'. Optionally and as shown, the bases 102', 104' of the splint 100' cover essentially all of the lingual surfaces of the teeth 130, 132, providing an increased surface area for attachment and enhanced bond reliability. While the teeth 130, 132 are adjacent teeth as shown here, this need not be the case. In some embodiments, for example, the connector beam 120' of the splint 100' could extend over the lingual surfaces of one or more intermediate teeth without being directly bonded to them. Also, the splint 100' can be bonded to three or more teeth in a consecutive manner if even greater anchorage is desired by the treating professional.

Finite Element Analysis

To better understand the result of having the connector beam contacting respective bases of the splint at locations remote from (as opposed to adjacent to) the outer edge of the base, finite element analysis (FEA) was used to simulate the three-dimensional (3D) stress profiles of seven different splint configurations, shown in FIGS. 6(a)-6(g). The FEA was performed on 3D models of the splints using ANSYS brand simulation software (v. 13, available from ANSYS Inc., Canonsburg, Pa.). Each of the splint configurations included bases that were adhesively bonded to virtual first and second bicuspid teeth, and in some cases, the first molar tooth. In this model, the teeth were surrounded by periodontal ligaments, which connected each tooth to its surrounding bone. The adhesive pad connecting each base to its underlying tooth had a defined thickness of 0.127 millimeters. The thickness of the periodontal ligaments ("PDL") was defined to be 0.15 millimeters for the bicuspid teeth and 0.20 millimeters for the first molar tooth. The thickness of the splint itself was defined as 0.508 millimeters, and the splint has a generally constant cross-sectional shape.

The analysis also made certain assumptions concerning Young's Modulus and Poisson Ratio of the component materials represented in the simulations. These values are provided in Table 1 below.

TABLE 1

Young's Modulus and Poisson Ratio used in finite element analyses

|  | Young's Modulus, MPa | Poisson's Ratio |
| --- | --- | --- |
| Adhesive | 1.17E+04 | 0.21 |
| Tooth | 1.96E+04 | 0.3 |
| Splint | 9.90E+04 | 0.3 |

The splints were then subjected to two different loading conditions to observe the resulting stress profiles: 1) a 178 N (40 lb.) occlusal force on the occlusal surface of the second bicuspid, and 2) an 89 N (20 lb.) occlusal force on the occlusal surface of the splint between the first and second bicuspids. The simulated force levels on the adhesive and PDL, and simulated principal stress imposed on splint, are shown for each splint configuration in Tables 2 and 3 below.

TABLE 2

FEA analysis of various splint configurations while applying a 178N occlusal force to the second bicuspid

| Splint concept | Description | Tooth | Force on adhesive, newtons | Force on PDL, newtons | Max. 1 P stress on splint, megapascals |
| --- | --- | --- | --- | --- | --- |
| A | 4-6 banded splint | first bicuspid | 49.4 | 49.8 | 159 |
|  |  | second bicuspid | 115.2 | 63.2 |  |
|  |  | first molar | 64.5 | 64.5 |  |
| B | 4-5 banded splint | first bicuspid | 60.9 | 61.8 | 159 |
|  |  | second bicuspid | 63.2 | 116.1 |  |
|  |  | first molar | — | — |  |
| C | 4-6 flexible splint, 0.51 × 0.64 mm (0.020 × 0.025 in.) | first bicuspid | 45.4 | 45.8 | 1320 |
|  |  | second bicuspid | 102.3 | 76.5 |  |
|  |  | first molar | 55.6 | 55.6 |  |
| D | 4-6 flexible splint, extended connection, 0.51 × 0.76 mm (0.020 × 0.030 in.) | first bicuspid | 19.6 | 19.6 | 765 |
|  |  | second bicuspid | 36.9 | 141.0 |  |
|  |  | first molar | 17.3 | 17.3 |  |
| E | 4-6 flexible splint, offset connection, 0.51 × 0.76 mm (0.020 × 0.030 in.) | first bicuspid | 12.0 | 12.0 | 552 |
|  |  | second bicuspid | 26.7 | 154.4 |  |
|  |  | first molar | 13.3 | 13.3 |  |
| F | 4-5 flexible splint, offset connection, 0.51 × 0.76 mm (0.020 × 0.030 in.) | first bicuspid | 22.2 | 22.7 | 710 |
|  |  | second bicuspid | 24.5 | 155.2 |  |
|  |  | first molar | — | — |  |
| G | 4-5 flexible splint, non-prismatic | first bicuspid | 8.4 | 8.9 | 358 |
|  |  | second bicuspid | 10.7 | 169.0 |  |
|  |  | first molar | — | — |  |

TABLE 3

FEA analysis of various splint configurations while applying an 89N occlusal force to the splint between the first and second bicuspids

| Splint concept | Description | Tooth | Force on adhesive, newtons | Force on PDL, newtons | Max. 1 P stress on splint, megapascals |
|---|---|---|---|---|---|
| A | 4-6 banded splint | first bicuspid | 37.4 | 37.8 | 179 |
|   |   | second bicuspid | 26.7 | 27.1 |   |
|   |   | first molar | 23.6 | 23.6 |   |
| B | 4-5 banded splint | first bicuspid | 43.6 | 44.5 | 228 |
|   |   | second bicuspid | 43.6 | 44.5 |   |
|   |   | first molar | — | — |   |
| C | 4-6 flexible splint, 0.51 × 0.64 mm (0.020 × 0.025 in.) | first bicuspid | 40.0 | 40.5 | 614 |
|   |   | second bicuspid | 29.8 | 30.2 |   |
|   |   | first molar | 18.2 | 18.2 |   |
| D | 4-6 flexible splint, extended connection, 0.51 × 0.76 mm (0.020 × 0.030 in.) | first bicuspid | 44.5 | 44.5 | 676 |
|   |   | second bicuspid | 39.1 | 39.1 |   |
|   |   | first molar | 5.3 | 5.3 |   |
| E | 4-6 flexible splint, offset connection, 0.51 × 0.76 mm (0.020 × 0.030 in.) | first bicuspid | 49.4 | 50.3 | 869 |
|   |   | second bicuspid | 34.7 | 35.6 |   |
|   |   | first molar | 3.1 | 3.1 |   |
| F | 4-5 flexible splint, offset connection, 0.51 × 0.76 mm (0.020 × 0.030 in.) | first bicuspid | 44.0 | 44.9 | 462 |
|   |   | second bicuspid | 43.1 | 44.0 |   |
|   |   | first molar | — | — |   |
| G | 4-5 flexible splint, non-prismatic | first bicuspid | 42.3 | 43.6 | 579 |
|   |   | second bicuspid | 44.0 | 45.4 |   |
|   |   | first molar | — | — |   |

The FEA showed significant differences in force and stress levels amongst concepts A-G, particularly in response to occlusal forces to the second bicuspid as shown in Table 2. Referring to the results obtained for concepts A, B, and C in Table 2 above, the application of about 178 N (40 lbs.) of bite force to the second bicuspid generated a force on the adhesive ranging from about 11 to 115 N. As to concepts D and E, the inclusion of either a 0.51×0.76 mm or 0.51×0.76 mm connector beam reduced the force on the adhesive to less than 40 N (9 lbs.), with the majority of the force absorbed by the PDL. However, the stresses on the connector beams are still higher than those in concepts A and B. Concept G transmitted the lowest force to the adhesive of 10.7 N, while also showing decreased stress on the splint compared with other flexible splint concepts. Concept G also appeared to impart greater forces to the PDL, up to about 169 N.

Figure 7:
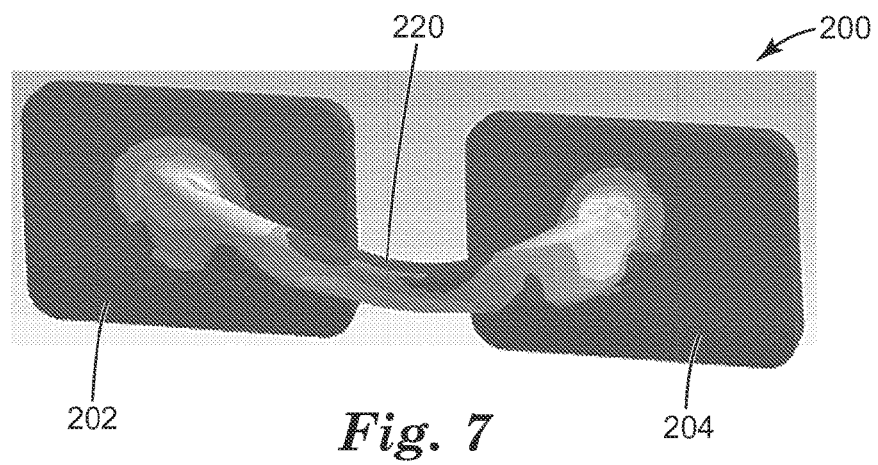
FIG. 7 shows a finite element analysis of a splint according to still another embodiment, showing a simulated stress distribution from one angle.
Figure 8:
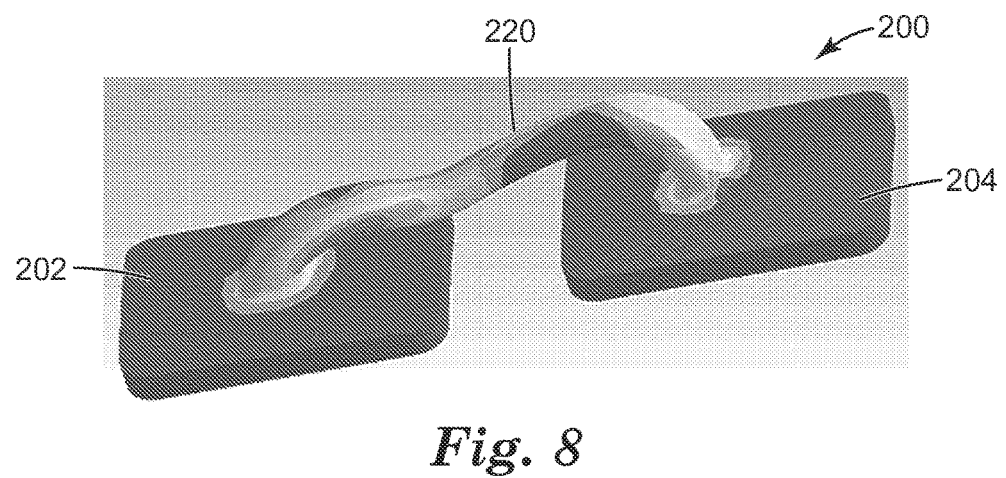
FIG. 8 shows a finite element analysis of the splint of FIG. 7, showing a simulated stress distribution from another angle.

FIGS. 7 and 8 show the simulated stress profile obtained for a simulated splint 200 (similar to splint concept G above). As shown, the splint 200 has bonding bases 202, 204 and includes a connector beam 220, with a cross-sectional area increasing toward its ends and decreasing toward its midpoint. In this concept, both the occlusal-gingival and facial-lingual components of the cross-sectional area vary along the longitudinal axis of the connector beam 220. FIGS. 7 and 8 show the distribution of the maximum principal stress from the ends of the connector beam toward the center of the connector beam 220. Areas of relatively high stress are indicated by darker shading, while areas of relatively low stress are indicated by lighter shading. The simulation showed that the beam 220 has a geometry that allows stress to be spread over a significant length of the beam, rather than being concentrated at its ends. Optionally, the configuration of the splint 200 can be further modified such that that the locations subjected to the highest levels of stress are provided with an enlarged cross-section to strengthen the splint 200 in locations where failure is most likely to occur.

EXAMPLES

Objects and advantages of the provided orthodontic splints are further illustrated by the following examples.

As used herein,

"SIL" refers to SIL brand silane primer, provided by 3M ESPE in St. Paul, Minn.;

"Concise" refers to CONCISE brand orthodontic chemical cure adhesive (REF 196-002 & 196-003), provided by 3M Unitek in Monrovia, Calif.; and "Rocatec Plus" refers to a ROCATEC brand Jr. blasting module using ROCATEC brand Plus media, both provided by 3M Company in St. Paul, Minn.

Splint Fabrication

Splints were manufactured using a "lost-wax" investment casting procedure, similar to those described in U.S. Pat. No. 6,776,614 (Wiechmann, et al.). In brief, the procedure begins with obtaining a 3D model of the splint configuration, as shown for example in FIG. 2. The 3D model was then exported to a rapid prototyping machine (a 3D printer) that constructed, layer-by-layer, a resin model of the splint. After printing, the resin model is used as a core in an investment casting process, where the model is embedded in cement and then melted to afford a negative mold. The negative mold is used to cast the final splint from gold alloy, after which the splint is removed by quenching the mold in water.

Splint Bonding Procedure

Each splint was bonded to two stainless steel rings having convex, knurled surfaces and positioned side-to-side. Each ring accommodated a respective base of the splint. The bonding surface of each base was sandblasted with Rocatec Plus (110 micrometer diameter silica, coated with aluminum oxide) according to manufacturer's instructions. A thin layer of SIL was then lightly brushed onto the sandblasted surfaces according to manufacturer's instructions.

The splint was then bonded to the knurled rings using CONCISE in accordance with manufacturer instructions.

Fracture Test Procedure

Debonding was conducted on each test specimen using a Q-TEST brand 5 Universal Test Machine (from MTS in Eden Prairie, Minn.) outfitted with a 1000 newton load cell.

Once the splint to be tested has been bonded to the pair of knurled rings, the rings were mounted to a two-part fixture and subjected to a simple displacement test. In this test, the first part of the fixture is held in a fixed position, while the second part is translated upward by the Test Machine at a fixed crosshead speed of 2.54 millimeters/second (0.1 inches/second). Crosshead displacement and load were continuously recorded until splint failure occurred. Failure was defined as either debonding, fracture, or substantial permanent deformation of the splint. The maximum force, and displacement at the maximum force, were then recorded for the test run.

Depending on the orientation of the rings in the fixture, the splint can be tested either in the facial-lingual direction or the occlusal-gingival direction. Facial-lingual fracture testing was conducted by orienting the rings such that the bonding surfaces of the splint were approximately parallel to the direction of the displacement. Occlusal-gingival testing was conducted by rotating the rings 90 degrees such that the bonding surfaces are approximately perpendicular to the direction of displacement. Since the splints were asymmetric when tested in the facial-lingual configuration, the orientation of the splint was flipped to provide an average measurement reflecting the results for both orientations.

Examples 1-2 and Comparative CE-1

Facial-lingual fracture testing was performed on various splint samples according to the Fracture Test Procedure above. This test examines a failure mode in which one tooth shifts in along a facial-lingual direction relative to its neighbor. Examples 1 and Example 2 were fabricated based on the splint configuration in FIGS. 6-7. Examples 1 and 2 differed in that the former used a SOLIDSCAPE brand 3D printer (from Stratasys, Eden Prairie, Minn.), while the latter used a PERFACTORY brand 3D printer (from EnvisionTEC GmbH, Gladbeck, GERMANY). Comparative CE-1 used a band splint configuration shown in FIG. 1 made using the SOLIDSCAPE brand printer. The results of these tests are shown in Table 4 below. As further noted below, some but not all splints debonded entirely from one of the rings during testing.

TABLE 4

Maximum displacement and force in facial-lingual directions

| Example/ Comparative | No. of samples | Average displacement at failure (millimeters) | Average load at failure (newtons) | Notes |
|---|---|---|---|---|
| 1 | 5 | 2.06 | 71.2 | 2 of 5 debonded |
| 2 | 12 | 2.41 | 104 | 3 of 12 debonded |
| CE-1 | 7 | 0.117 | 17.5 | |

Examples 3-4 and Comparative CE-2

Occlusal-gingival fracture testing was performed in Examples 3-4 and CE-2. In these measurements, each splint was oriented in the fixture to simulate the failure mode caused by occlusal-gingival movement of one tooth relative to its neighbor. Like Examples 1 and 2 above, Examples 3 and 4 were prepared using a SOLIDSCAPE brand 3D printer and a PERFACTORY brand 3D printer, respectively. Fracture test results for Examples 3 and 4 are given in Table 5 below.

TABLE 5

Maximum displacement and force in occlusal-gingival directions

| Example/ Comparative | No. of samples | Average displacement at failure (millimeters) | Average load at failure (newtons) | Notes |
|---|---|---|---|---|
| 3 | 5 | 0.240 | 105 | |
| 4 | 3 | 2.14 | 72.1 | 1 of 3 debonded |
| CE-2 | 5 | 1.60 | 66.7 | 1 of 5 debonded |

Examples 5-6

Fatigue testing was then conducted on the splints of Examples 1 and 2, respectively, in an occlusal-gingival orientation. In these tests, all splints tested survived 500 cycles at a strain amplitude of ±0.30 mm. When the amplitude was subsequently increased to ±0.45 mm, all samples eventually failed. The average cycle life of each Example is shown in Table 6 below.

TABLE 6

Fatigue test results

| Example/ Comparative | N | Cycles at ±0.30 millimeters | Cycles at ±0.45 millimeters |
|---|---|---|---|
| 5 | 3 | 500* | 142 |
| 6 | 10 | 500* | 149 |

*without failure

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

What is claimed is:

1. An orthodontic splint comprising:
a first base and second base, each base having a bonding surface for attachment to a respective tooth and an outer edge extending along at least a portion of the bonding surface as viewed from a direction generally perpendicular to the bonding surface, each base including an outer surface directly opposite the bonding surface; and
an elongated connector beam having a cross-sectional dimension that generally increases with increasing proximity to the nearer of the first or second base, the connector beam attached to the outer surface of each base along locations remote from the outer edge of the base,
wherein the connector beam extends outwardly away from each base at an angle ranging from 10 to 90 degrees relative to a tangent plane where the longitudinal axis of the connector beam intersects a respective outer surface of the base.

2. The splint of claim 1, wherein each end of the connector beam generally extends outwardly away from each base at an angle ranging from 30 to 90 degrees relative to a tangent plane where the longitudinal axis of the connector beam intersects a respective outer surface of the base.

3. The splint of claim 1, wherein the cross-sectional dimension is aligned along a generally occlusal-gingival direction.

4. The splint of claim 1, wherein at least a portion of the connector beam has a longitudinal axis and a generally rectangular cross-section as taken along a reference plane perpendicular to the longitudinal axis.

5. The splint of claim 4, wherein the cross-sectional dimension is aligned along the long axis of the rectangular cross-section.

6. The splint of claim 1, wherein the first and second bases and connector beam have a unitary construction.

7. The splint of claim 1, wherein the first and second bases have configurations for bonding to adjacent teeth.

8. The splint of claim 1, wherein the ratio between the cross-sectional dimension of the connector beam at its widest point and that of the connector beam at its narrowest point is no greater than 3.

9. The splint of claim 1, wherein the outer edge of each base fully surrounds its respective bonding surface.

10. The splint of claim 1, further comprising a bracket for coupling the splint to an ancillary appliance.

11. The splint of claim 10, wherein the ancillary appliance is selected from an archwire, force module, and transpalatal device.

12. A method of maintaining a fixed spatial relationship between a first and second tooth during orthodontic treatment, the method comprising:
    coupling a first base of an orthodontic splint to the first tooth; and
    coupling a second base of the orthodontic splint to the second tooth,
wherein each base has a bonding surface for attachment to its respective tooth and an outer edge extending along at least a portion of the bonding surface as viewed from a direction generally perpendicular to the bonding surface, each base including an outer surface directly opposite the bonding surface, wherein the orthodontic splint comprises an elongated connector beam having a cross-sectional dimension that generally increases with increasing proximity to the nearer of the first or second base, the connector beam attached to the outer surface of each base along locations remote from the outer edge of the base, and wherein the connector beam extends outwardly away from each base at an angle ranging from 10 to 90 degrees relative to a tangent plane where the longitudinal axis of the connector beam intersects a respective outer surface of the base.

13. An orthodontic splint comprising:
    a first base and second base, each base having a bonding surface for attachment to a respective tooth surface and an outer edge extending along at least a portion of the bonding surface as viewed from a direction generally perpendicular to the bonding surface each base including an outer surface directly opposite the bonding surface; and
    a resilient, elongated connector beam having a longitudinal midpoint and a cross-sectional dimension that generally decreases when approaching the midpoint from either the first or second base, the connector beam attached to each base in a position on the outer surface remote from the outer edge of the base, wherein the connector beam extends outwardly away from each base at an angle ranging from 10 to 90 degrees relative to a tangent plane where the longitudinal axis of the connector beam intersects a respective outer surface of the base.

14. The splint of claim 13, wherein at least a portion of the connector beam has a longitudinal axis and a generally rectangular cross-section as taken along a reference plane perpendicular to the longitudinal axis.

15. The splint of claim 14, wherein the cross-sectional dimension is aligned along the long axis of the rectangular cross-section.

16. The splint of claim 13, wherein the ratio between the cross-section dimension of the connector beam at its widest point and that of the connector beam at its narrowest point is no greater than 3.

17. The splint of claim 13 further comprising a bracket for coupling the splint to an ancillary appliance selected from an archwire, force module, and transpalatal device.

* * * * *